US00PP23726P3

(12) United States Plant Patent
Clingeleffer

(10) Patent No.: US PP23,726 P3
(45) Date of Patent: Jul. 9, 2013

(54) GRAPEVINE PLANT NAMED 'M 44-14'

(50) Latin Name: *Vitis hybrida*
Varietal Denomination: M 44-14

(75) Inventor: Peter R. Clingeleffer, Glen Osmond (AU)

(73) Assignee: Commonwealth Scientific and Industrial Research Organisation, Australian Capital Territory (AU)

( * ) Notice: Subject to any disclaimer, the term of this patent is extended or adjusted under 35 U.S.C. 154(b) by 0 days.

(21) Appl. No.: 13/137,135

(22) Filed: Jul. 22, 2011

(65) Prior Publication Data

US 2012/0255075 P1 Oct. 4, 2012

(30) Foreign Application Priority Data

Mar. 28, 2011 (AU) ..... PBR 2011055

(51) Int. Cl.
*A01H 5/00* (2006.01)

(52) U.S. Cl.
USPC ..... Plt./207

(58) Field of Classification Search
USPC ..... Plt./207
See application file for complete search history.

*Primary Examiner* — Annette Para
(74) *Attorney, Agent, or Firm* — Buchanan Ingersoll & Rooney PC

(57) ABSTRACT

A new and distinct variety of diploid grapevine is provided which abundantly forms late-ripening large bunches of sweet firm crisp substantially elliptic-to-obovate large berries which develop a green to yellow-golden coloration at maturity and provide the capability for long-term storage. The plant is particularly well suited for the production of table grapes. The fruit also can be used as a dried vine fruit or for the making of wine.

3 Drawing Sheets

Figure 1:
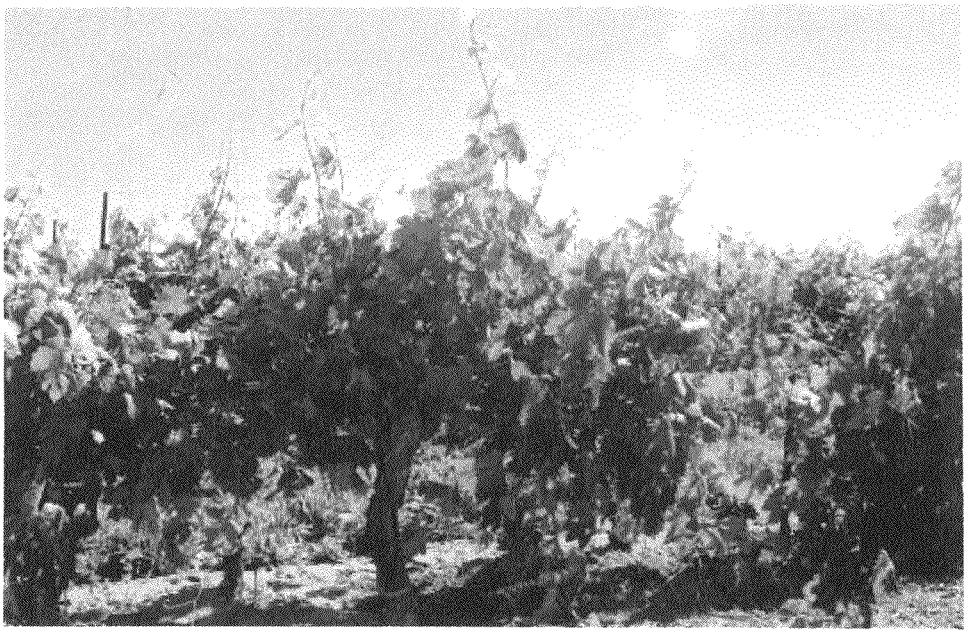

Botanical/commercial classification: *Vitis hybrida*/Grapevine.

Varietal denomination: cv. M 44-14.

BACKGROUND OF THE VARIETY

The new diploid grapevine variety of the present invention was created during the course of a grapevine breeding program that was carried out in Australia wherein two parents were crossed which previously had been studied in the hope that they would contribute the desired characteristics. The female parent (i.e., seed parent) was the 'Hunisa' variety (non-patented in the United States). The male parent (i.e., pollen parent) was a complex unreleased selection created in Australia at the Commonwealth Scientific and Industrial Research Organisation (CSIRO) and designated 'M 37-02' (non-patented in the United States). 'M 37-02' was bred by crossing a selection of *Vitis longii* with another unreleased selection of the same entity designated 'M 39-11' (non-patented in the United States) which was an open-pollinated seedling of the *Vitis vinifera* 'Danogue' variety (non-patented in the United States). The parentage of the new variety of the present invention can be summarized as follows:

'Hunisa' 'Danogue'

*Vitis vinifera* × [*Vitis longii* × (*Vitis vinifera* × *Vitis* spp.)].

The controlled cross that resulted in the production of the new variety of the present invention was carried out during Spring 1992 (Southern Hemisphere). Since the female parent was pollen infertile, its inflorescences were placed in pollen-proof bags before the flowers opened. The bags were removed at the appropriate time and pollen from the male parent was applied to the receptive stigma of the female parent. Such pollen had been collected from unopened flowers of male parent, and thereafter was dried in Petri dishes at 40° C. under conditions where contamination by other *Vitis* pollen was precluded. The resulting seeds from the cross were extracted from the fruits in Autumn 1993 (Southern Hemisphere) and were sown in a greenhouse while employing standard seed bed conditions. Emergent seedlings were transferred to standard potting mix and were maintained in pots under greenhouse conditions until they were planted in a vineyard during Spring 1993 (Southern Hemisphere). Thereafter, the plants were grown and evaluated while using standard grapevine cultivation conditions.

A single plant of the new variety was selected during 2002 from among the resulting siblings. The new variety was found to possess a combination of characteristics unlike that of its siblings and unlike that of either of the respective parent plants. The resulting plant has been carefully observed, tested and evaluated in replicated plantings and trials while growing on its own roots or when top-worked onto a range of grape rootstocks.

It was found that the new grapevine of the present invention displays the following combination of characteristics:

(a) displays high stenospermocarpic fruit production,
(b) forms in abundance late-ripening large bunches of sweet firm crisp substantially elliptic-to-obovate berries which develop a green to yellow-golden coloration at maturity and provide the capability for long-term storage, and
(c) is particularly well suited for the production of table grapes.

The new variety well meets the needs of the horticultural industry. It can be grown to advantage for the production of table grapes for fresh fruit consumption. It also may be used for the production of dried vine fruit, or for the making of wine. The new variety is capable of providing a late-season supply of quality grapes that well maintain their character under cool storage. Satisfactory storage qualities have been observed for up to three months and make possible the servicing of export markets as well as the domestic market. The berries possess an attractive distinctive waxy bloom that serves to enhance their visual appeal, provided care is given during handling.

The attractive berries are substantially elliptic-to-obovate in configuration with some tapering towards the pedicel end. Natural berries commonly weigh approximately 4 to 5 g, are approximately 18 mm in diameter, and are approximately 24 mm in length. Under highly managed conditions with bunch trimming and thinning, berry weights of 6 to 10 g, berry diameters of 20 to 25 mm and berry lengths of 25 to 30 mm have been observed. Berry size may be increased by the application of growth regulators including combinations of 2 to 8 ppm gibberellic acid and 1.5 to 4.5 ppm of N-(2-chloro-4-pyridinyl)-N'-phenylurea.

In order to optimize fruit quality, shoots may be removed from vines and bunches subjected to thinning and trimming. It has been found for better results that five to seven lateral shoots with bunches should be retained on each vine with the removal of all non-fruitful shoots in order to reduce the density of the plant canopy. It has been found that vines of the new variety are very fruitful even in sub-tropical environments and can be spur pruned so as to reduce production costs commonly associated with cane pruning.

It has been found that best results are achieved when harvesting is delayed until the juice sugar concentration reaches approximately 19.5° Brix or until the sugar-to-acid ratio of the juice is greater than approximately 32:1. At this stage of ripening, the skin of the berries is light green to pale cream in coloration.

The new variety of the present invention can be readily distinguished from its parental varieties and other presently available grape varieties. The 'Hunisa' female parent forms seeded large red berries, displays leaves and fruit that are more susceptible to downy mildew (*Plasmopara vitcola*), and exhibits poorer fruit set in large plantings. The 'M 37-02' male parent forms seeded small green berries and leaves that are more susceptible to downy mildew. When the new variety is compared to the widely grown 'Sultana' table grape variety, sometimes known as 'Thompson Seedless' (non-patented in the United States), it is found that the new variety ripens later, forms larger natural fruit in the absence of hormone application, and displays superior fruit storage characteristics.

The new variety of the present invention has been found to undergo asexual propagation in Australia, by a number of routes including budding, top-working, and the rooting of cuttings. Accordingly, the new variety has been found to undergo asexual propagation in a true-to-type manner. During such propagation, the new variety has been found to be compatible with a wide range of rootstocks.

The new variety was named 'M 44-14'.

DETAILED DESCRIPTION OF PHOTOGRAPHS

The accompanying photographs show, as nearly true as it is reasonably possible to make the same in color illustrations of this character, typical specimens of the new variety.

Figure 2:
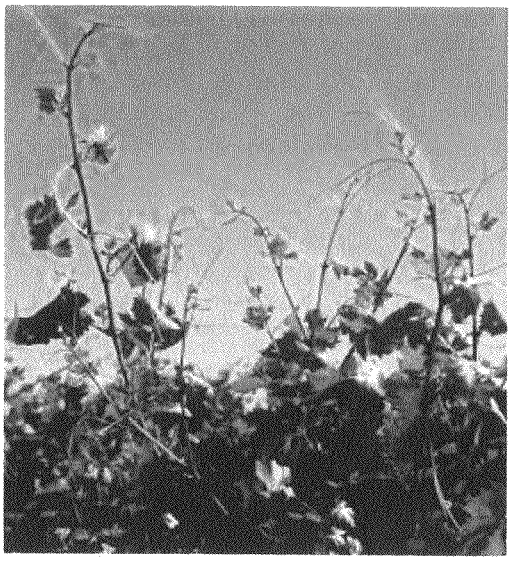
Figure 3:
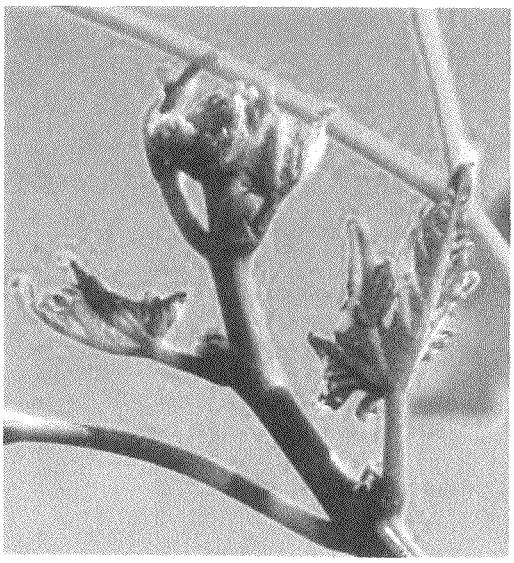
Figure 4:
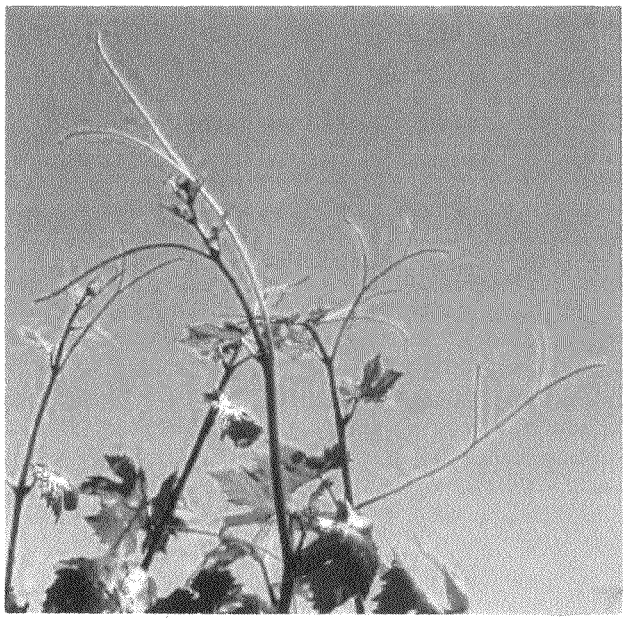
Figure 5:
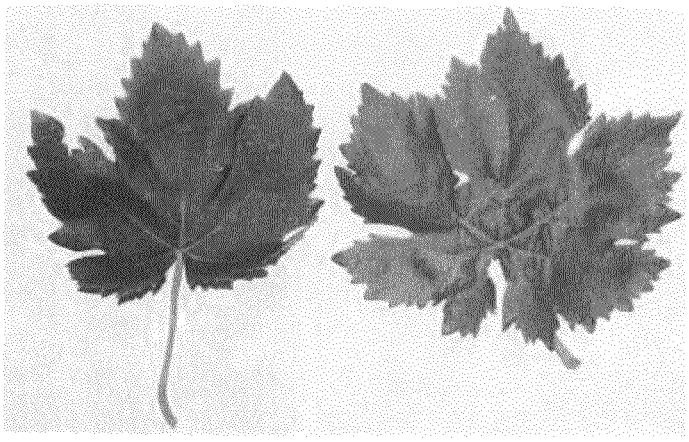
Figure 6:
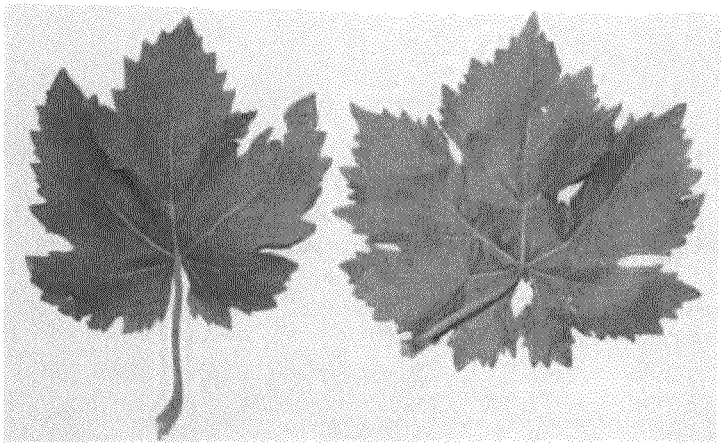
Figure 7:
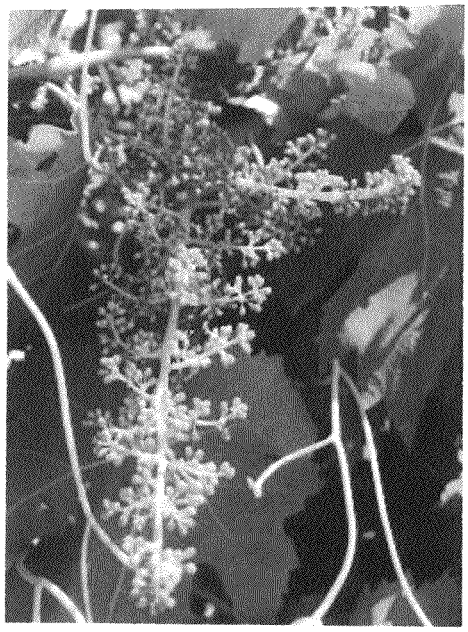
Figure 8:
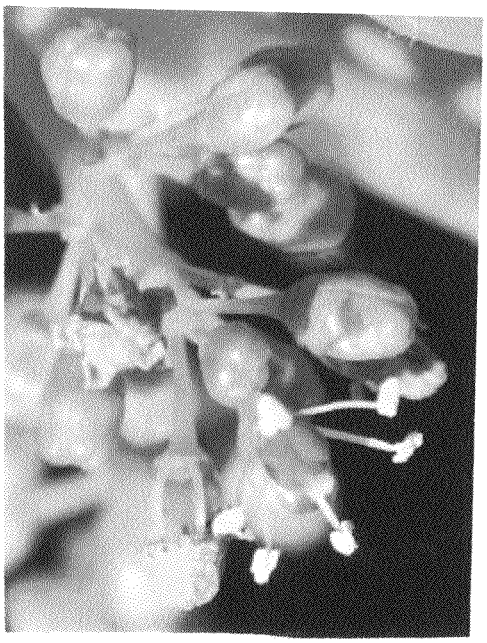
Figure 9:
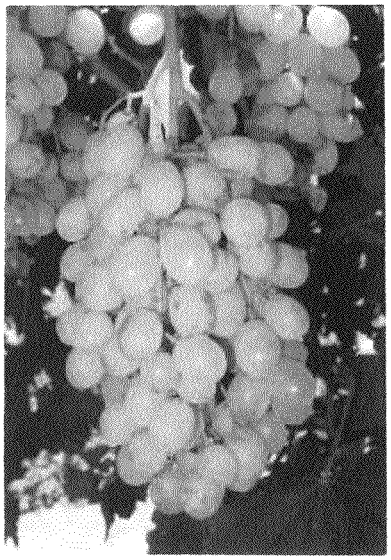
Figure 10:
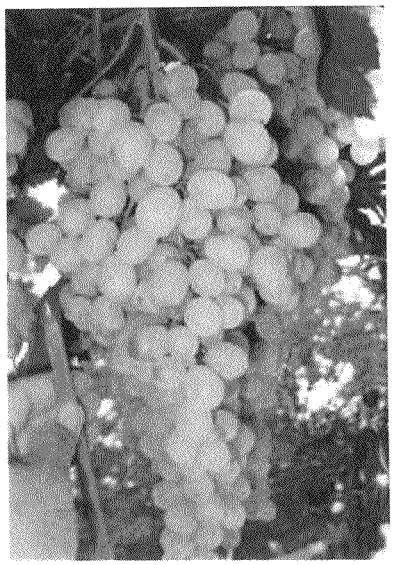

FIG. 1—illustrates the typical vine growth habit wherein the formation of a dense canopy is illustrated which is aided by strong tendrils;

FIG. 2—illustrates young shoots wherein some tendrils are present;

FIG. 3—illustrates a close view of a young shoot tip;

FIG. 4—illustrates a close view of typical young shoots with extending tendrils;

FIG. 5—illustrates a pair of typical mature leaves (adaxial surfaces);

FIG. 6—illustrates a pair of typical mature leaves (abaxial surfaces);

FIG. 7—illustrates a typical inflorescence;

FIG. 8—illustrates a typical inflorescence wherein individual flowers are shown;

FIG. 9—illustrates a close view of a typical mature berry cluster produced on an own-rooted vine showing the natural berry characteristics; and FIG. 10—illustrates a close view of a typical berry cluster produced on a vine grafted on a rootstock.

DETAILED DESCRIPTION

The following description is based upon the observation of representative mature six-year-old plants of the new variety while growing on their own roots in Australia. Color terms are to be accorded their customary dictionary significance. Color terminology is in accordance with The R.H.S. Colour Chart (1966 Edition or equivalent) of The Royal Horticultural Society (London) in association with the Flower Council of Holland (Leiden).

Vine:

*Young shoots*.—Time of bud burst: late. Form of tip: half-open to wide-open. Color: Yellow-Green Group 146B soon after burst. Anthocyanin coloration of tip: absent. Density of prostrate hairs on tip: sparse. Density of erect hairs on tip: very sparse.

*Mature shoots*.—Attitude: substantially erect. Color of dorsal side of internode: Green Group 139C and striped with Greyed-Brown Group 177B with some Greyed-Orange Group 174B. Color of ventral side of internode: Green Group 139C. Color of dorsal side of node: Yellow-Green Group 144B striped with Greyed-Brown Group 177B. Color of ventral side of node: Green Group 139C. Density of erect hairs on node: absent. Erect hairs on internode: absent. Density of prostrate hairs on node: very sparse. Density of prostrate hairs on internode: very sparse. Number of consecutive tendrils: commonly up to two per standard UPOV description. Length of tendril: medium, with lengths of 19 to 21 cm on average commonly being observed. Length of internodes: medium, commonly approximately 6 to 8 cm. Growth of axillary shoots: weak.

*Young leaves*.—Color of upper surface: Yellow-Green Group 146B. Color of under surface: Yellow-Green Group 146B. Density of prostrate hairs between veins: absent to very sparse. Density of erect hairs between veins: absent. Density of prostrate hairs on main veins: very sparse to sparse. Density of erect hairs on main veins: absent to very sparse.

*Mature leaves*.—Blade length: commonly approximately 1.2 cm on average. Blade width: commonly approximately 1.6 cm on average. Color of upper surface: Green Group 137B. Color of under surface:

Green Group 137C. Blade shape: pentagonal. Lobe number: five. Anthocyanin coloration of main veins on upper surface: absent. Profile: flat to V-shaped. Blistering of blade upper surface: absent. Shape of teeth: both sides straight (rectilinear). Length of teeth: commonly approximately 9 mm on average. Width of teeth: commonly approximately 11 mm on average. General shape of petiole sinus: wide to half open. Tooth at petiole sinus: present. Petiole length: commonly approximately 1.2 cm on average. Petiole sinus limited by veins: absent. Shape of upper lateral sinus lobes: slightly overlapping. Depth of upper lateral sinus: deep. Density of prostrate hairs: absent. Density of prostrate hairs between veins: absent. Density of erect hairs between veins: absent. Density of prostrate hairs on main veins: absent. Density of erect hairs on main veins: absent. Length of petiole compared to middle vein: slightly shorter.

*Woody shoots*.—Surface: striate, with stripes of Yellow Group 11B. Primary color: commonly Greyed-Orange Group 177B.

Inflorescence:

*Buds*.—Color: Yellow-Green Group 148B when unopened.

*Flowers*.—Number per shoot: commonly approximately 1.1 to 2 on average. Sex: male and female parts fully developed. Ovary color: Green Group 137A following capfall.

*Peduncle*.—Length: 4 cm on average. Diameter: commonly approximately 5 to 6 mm on average.

*Bunches*.—Productivity: high. Percentage of berry set: low, and commonly 20 to 30 percent. Single bunch weight: medium to high, and commonly 450 to 950 g on average. Length: long to very long. Density: relatively loose.

*Berries*.—Ripening season: late in the Murray Valley of Australia. Size: medium. Weight: medium, commonly 3 to 5 g per single berry on average. Shape: elliptic to obovate. Skin thickness: medium. Presence of seeds: seedless to rudimentary formation. Skin color (with bloom: Yellow-Green Group 148B. Skin color (without bloom): Yellow-Green Group 152B. Flesh color: Yellow-Green Group 152B. Anthocyanin coloration of flesh: absent. Juiciness of flesh: very slightly juicy. Firmness of flesh: relatively firm. Particular flavor: none. Pedicel length: intermediate. Ease of detachment from pedicel: somewhat difficult. Sugar content of must: high, commonly near 21 percent. Acid content of must: low (0.6 percent tartrate).

*Seeds*.—Commonly absent, or soft/rudimentary when rarely present.

Biotic stress susceptibility: During evaluation to date the following has been observed:

*Botrytis cinerea*.—Noble Rot — low on leaves and low on fruit.

*Plasmopara viticola*.—Downy Mildew — medium on leaves and low on fruit.

*Uncinula necator*.—Powdery Mildew — medium on leaves and medium on fruit.

*Elsinoe ampelina*.—Anthracnose — never observed.

*Entypa lata*.—Dieback — never observed.

Plants of the new 'M 44-14' variety have not been observed under all possible environmental conditions to date. Accordingly, it is possible that the phenotypic expression may vary somewhat with changes in light intensity and duration, cultural practices, and other environmental conditions.

I claim:

1. A new and distinct grape plant characterized by the following combination of characteristics:

(a) displays high stenospermocarpic fruit production, (b) forms in abundance late-ripening large bunches of sweet firm crisp substantially elliptic-to-obovate berries which develop a green to yellow-golden coloration at maturity and provide the capability for long-term storage, and (c) is particularly well suited for the production of table grapes;

substantially as shown and described.

* * * * *